United States Patent [19]
DiPoto et al.

[11] Patent Number: 5,957,953
[45] Date of Patent: Sep. 28, 1999

[54] EXPANDABLE SUTURE ANCHOR

[75] Inventors: Gene P. DiPoto, Upton; Denise D. Fitzpatrick, Boxborough; Jeffrey Cerier; José E. Lizardi, both of Franklin, all of Mass.; Russell Warren, New York, N.Y.

[73] Assignee: Smith & Nephew, Inc., Memphis, Tenn.

[21] Appl. No.: 08/602,977

[22] Filed: Feb. 16, 1996

[51] Int. Cl.⁶ .................................................. A61B 17/04
[52] U.S. Cl. ............................................ 606/232; 606/72
[58] Field of Search ................................ 606/72, 73, 232

[56] References Cited

U.S. PATENT DOCUMENTS

| | | |
|---|---|---|
| 2,562,419 | 7/1951 | Ferris . |
| 2,665,597 | 1/1954 | Hill ............................................... 77/2 |
| 2,699,774 | 1/1955 | Livingston ................................. 128/92 |
| 3,036,482 | 5/1962 | Kenworthy et al. . |
| 4,013,071 | 3/1977 | Rosenberg . |
| 4,140,111 | 2/1979 | Morrill . |
| 4,259,072 | 3/1981 | Hirabayashi et al. . |
| 4,287,807 | 9/1981 | Pacharis et al. ........................... 411/42 |
| 4,447,915 | 5/1984 | Weber .......................................... 3/1.9 |

(List continued on next page.)

FOREIGN PATENT DOCUMENTS

| | | |
|---|---|---|
| 0 270 704 | 12/1986 | European Pat. Off. . |
| 0 340 159 | 3/1989 | European Pat. Off. . |
| 0 409 364 A2 | 1/1991 | European Pat. Off. . |
| 0 502 509 A1 | 9/1992 | European Pat. Off. . |
| 0 574 707 A1 | 12/1993 | European Pat. Off. . |
| 0 591 991 A2 | 4/1994 | European Pat. Off. . |
| 2 084 468 | 4/1982 | United Kingdom . |

OTHER PUBLICATIONS

Innovasive Devices, Inc., "Product Focus ROC Fastener System," "Selecting a Fastener for Hard Bond: Beyond Pull Out Strength", Feb., 1995.

*Primary Examiner*—Michael Buiz
*Assistant Examiner*—Daphna Shai
*Attorney, Agent, or Firm*—Fish & Richardson P.C.

[57] ABSTRACT

An adjustably expandable suture anchor is provided. The suture anchor includes a pair of members, one of which includes a suture mount, which are configured to be secured together in a selected one of a plurality of positions to cause one of the members to expand by an amount that corresponds to the selected position. In one embodiment, the expandable member is an outer member, and the other member is an inner member which is progressively insertable into an opening in a body of the outer member and securable in the selected position therein. For example, the inner member is threaded into the outer member body or is inserted into the body in ratchet-like fashion. As the inner member is inserted distally into the outer member, an exterior enlargement on the inner member engages a plurality of arms which extend proximally from body, and causes the arms to progressively expand radially outwardly. Because the amount of expansion is adjustable, the suture anchor can be customized to provide the proper amount of fixation for the quality of the bone in which the anchor is installed. For example, when used in relatively soft bone tissue, the suture anchor can be expanded to a greater degree than might be required in harder bone tissue to obtain secure fixation.

59 Claims, 6 Drawing Sheets

U.S. PATENT DOCUMENTS

| | | | |
|---|---|---|---|
| 4,450,834 | 5/1984 | Fischer . | |
| 4,450,835 | 5/1984 | Asnis et al. . | |
| 4,476,861 | 10/1984 | Dimakos et al. | 128/303 |
| 4,590,928 | 5/1986 | Hunt et al. . | |
| 4,632,100 | 12/1986 | Somers et al. . | |
| 4,632,101 | 12/1986 | Freedland . | |
| 4,716,893 | 1/1988 | Fischer et al. . | |
| 4,721,103 | 1/1988 | Freedland . | |
| 4,772,286 | 9/1988 | Goble et al. | 623/13 |
| 4,778,468 | 10/1988 | Hunt et al. . | |
| 4,834,752 | 5/1989 | Van Kampen . | |
| 4,851,005 | 7/1989 | Hunt et al. . | |
| 4,858,603 | 8/1989 | Clemow et al. . | |
| 4,870,957 | 10/1989 | Goble et al. . | |
| 4,924,865 | 5/1990 | Bays et al. . | |
| 4,940,467 | 7/1990 | Tronzo . | |
| 4,944,742 | 7/1990 | Clemow et al. . | |
| 4,976,715 | 12/1990 | Bays et al. . | |
| 5,013,316 | 5/1991 | Goble et al. . | |
| 5,037,422 | 8/1991 | Hayhurst et al. . | |
| 5,084,050 | 1/1992 | Draenert . | |
| 5,129,906 | 7/1992 | Ross et al. . | |
| 5,176,682 | 1/1993 | Chow . | |
| 5,203,784 | 4/1993 | Ross et al. . | |
| 5,209,753 | 5/1993 | Biedermann et al. . | |
| 5,236,445 | 8/1993 | Hayhurst et al. | 606/232 |
| 5,268,001 | 12/1993 | Nicholson et al. . | |
| 5,354,298 | 10/1994 | Lee et al. . | |
| 5,380,334 | 1/1995 | Torrie et al. . | |
| 5,423,860 | 6/1995 | Lizardi et al. . | |
| 5,464,427 | 11/1995 | Curtis et al. | 606/72 |
| 5,480,403 | 1/1996 | Lee et al. | 606/72 |
| 5,486,197 | 1/1996 | Le et al. . | |

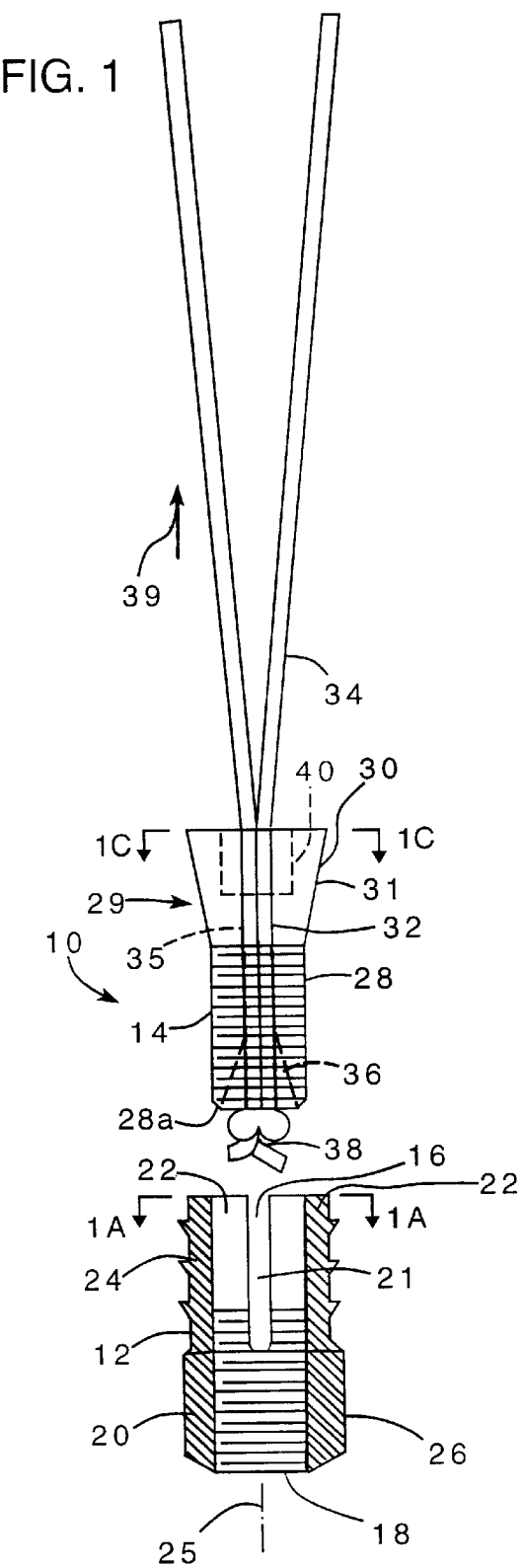
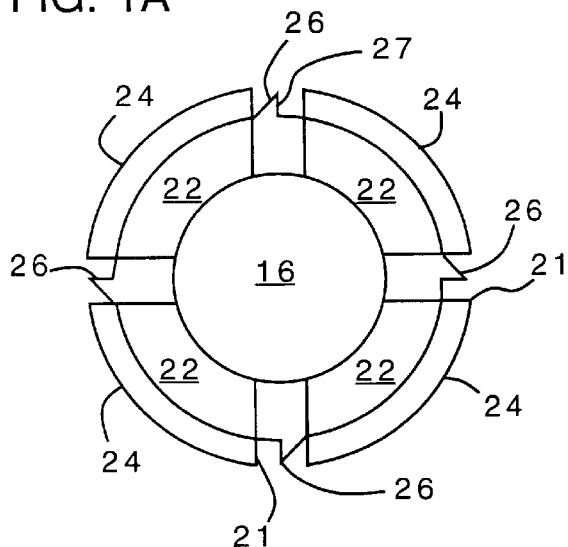
FIG. 1
FIG. 1A

FIG. 4A
FIG. 4
FIG. 5
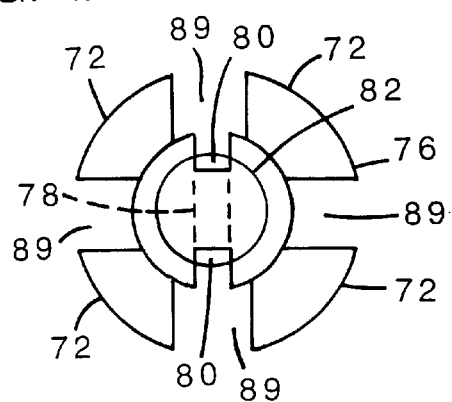
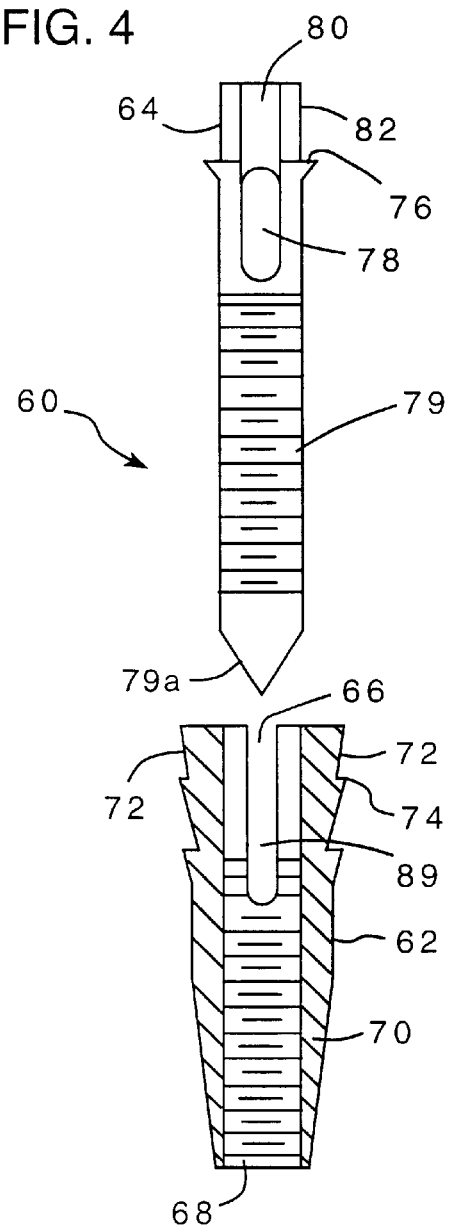
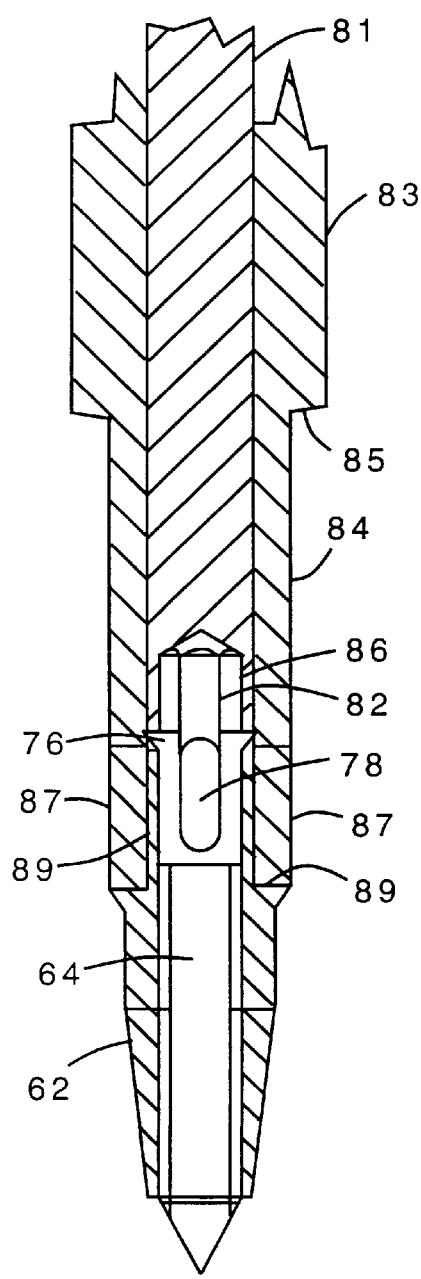

EXPANDABLE SUTURE ANCHOR

BACKGROUND OF THE INVENTION

This invention relates to suture anchors.

Suture anchors are used to mount suture to bone for subsequent attachment of ligaments, tendons, or other tissue. Some suture anchors are inserted into a pre-drilled hole in the bone, while others are "self-tapping" and are threaded into the bone through the bone surface. In either case, ridges which extend outwardly from the exterior surface of the suture anchor help retain the anchor in the bone tissue (in self-tapping anchors, the ridges are often the external threads).

SUMMARY OF THE INVENTION

This invention features an adjustably expandable suture anchor. Because the amount of expansion is adjustable, the suture anchor can be customized to provide the proper amount of fixation for the quality of the bone in which the anchor is installed. For example, when used in relatively soft bone tissue, the suture anchor can be expanded to a greater degree than might be required in harder bone tissue to obtain secure fixation. As a result, the suture anchor is useful for a wide variety of surgical procedures.

In one general aspect of the invention, the suture anchor comprises a pair of members, one of which includes a suture mount, that are configured to be secured together in a selected one of a plurality of positions to cause one of the members to expand by an amount that corresponds to the selected position.

Preferred embodiments may include one or more of the following features.

The expandable member comprises an outer member, and the other member is an inner member which is progressively insertable into an opening in the outer member and securable in the selected position therein. The outer member includes a body to which the inner member is secured, and an expandable portion configured to be expanded by the inner member. The opening is disposed through the expandable portion and the body along a longitudinal axis of the outer member.

Preferably, the expandable portion includes a plurality of arms which extend axially and proximally from the body. The arms are arranged around the periphery of the body and are circumferentially spaced by axially extending slots. In one embodiment, each slot includes an enlarged portion adjacent to the junction between the arms and the body. This allows the arms to be more readily expanded by the inner member.

The inner member is insertable into the opening at the proximal end of the outer member. An exterior enlargement on the inner member engages the arms and causes the arms to progressively expand radially outwardly as the inner member is inserted distally into the opening. In one embodiment, the enlargement tapers in size axially along inner member. For example, the enlargement is a conically shaped proximal end of the inner member. In another embodiment, the enlargement is a rib disposed on a portion of the exterior surface.

The suture anchor members can be secured together in a variety of ways. In one embodiment, the members are each provided with threads and are secured together by rotatably inserting the inner member into the outer member. The threads are located in the opening of the outer member body and on the distal end of the inner member. The threaded engagement between the inner and outer members allows the amount of expansion to be continuously adjusted according to the amount by which the inner member is rotated into the outer member.

In another embodiment, the inner and outer members are configured to engage each other in a ratchet-like fashion. This enables the outer member to be selectively expanded simply by advancing the inner member axially into the opening—no rotation is required. In this approach, circumferential grooves are arranged axially along the exterior surface of the inner member, and are progressively engaged by a projection in the body opening as the inner member is inserted axially into the outer member.

One or more transversely-oriented ridges are disposed on the exterior surface of the outer member arms. These ridges further assist in retention by enhancing the interference fit between the suture anchor and the bone. A series of axially-oriented ridges are arranged around the periphery of the body's exterior surface. The axial ridges are particularly useful in resisting rotation of the outer member in the embodiment in which the inner member is threaded into the outer member. The outer member can be configured for insertion into a pre-drilled bone hole, or not. In the latter case, the outer member includes threads on its exterior surface to ease insertion.

In one embodiment, the suture mount is on the inner member. For example, a suture receiving passage is arranged in the inner member along the longitudinal axis thereof. The passage is enlarged near the distal end of the inner member (such as by tapering the passage in width). Enlarging the distal portion of the passage allows a knot formed when, e.g., multiple sutures are tied together to be retracted into the interior of the inner member, thereby protecting the knot and the suture from damage when the suture anchor is emplaced and expanded within the bone.

Alternatively, the suture receiving passage in the inner member is oriented transversely to the inner member's longitudinal axis. A pair of axially oriented channels are provided in the exterior surface of the inner member adjacent to the open ends of the transverse passage; the channels receive suture which is passed through the passage and help protect the suture from being damaged by the interference fit between the suture anchor and bone. The channels also allow the user to slide the suture within the passage when the suture anchor is in place in the bone.

In another embodiment, the suture mount is disposed on the outer member. For example, distal end of the outer member is closed (and forms, e.g., a tapered tip), and a suture receiving passage is disposed in the closed distal end. The passage is oriented transversely to the longitudinal axis of the outer member and has a pair of open ends in an exterior surface of the outer member. A pair of axially-extending channels are disposed in the exterior surface adjacent to the open ends of the passage to receive suture. These channels are aligned with the slots between the expansion arms of the outer member to provide a path for suture between the suture anchor and the bone tissue.

Another aspect of the invention features a combination of the suture anchor and a driver for expanding the anchor in the bone.

Preferred embodiments may include the following features.

The driver and the proximal region of the inner member are configured to engage each other to allow the driver to transmit force to the inner member and insert it into the outer member. For example, in the embodiment in which the inner member threads into the outer member, the engagement (such as a socket in the proximal region of the inner member which receives a corresponding post on the driver) allows the driver to transmit torque to rotate the inner member. In embodiments in which the suture receiving passage is oriented axially through the inner member, an end of the passage opens at the socket. A suture passage in the driver communicates with the suture receiving passage in the inner member when the post is received in the socket.

The driver preferably includes a movable shaft disposed within an outer sleeve. The distal end of the outer sleeve is configured to engage the outer member within a plurality of axially extending slots between the arms of the outer member. The engagement between the outer sleeve and the outer member of the suture anchor aids in emplacing the outer member in the bone, and provides a way of keeping the outer member stationary while the inner member is being progressively inserted therein. The outer sleeve also includes an exterior shoulder positioned a selected distance proximally of the distal end. The shoulder limits the depth in which the suture anchor can be inserted into the bone.

The suture anchor is easy to use and can be securely attached in a wide variety of bone tissue. After the anchor is placed into the bone (either in a pre-drilled hole or by threading the anchor into the bone), the inner member is progressively advanced within the outer member until it expands the outer member by the desired amount.

One particularly useful method of using the suture anchor is to preselect a threshold amount of force that is to be exerted on the inner member during insertion, and measure the force (such as with a torque meter) during insertion. Insertion is stopped when the threshold force level is reached. This technique helps ensure that the outer member is expanded by the correct amount regardless of the density of the bone tissue. Thereafter, the suture anchor is held securely in place by the expanded outer member and the transverse ridges thereon.

Other features and advantages of the invention will be apparent from the following detailed description, and from the claims.

BRIEF DESCRIPTION OF THE DRAWINGS

FIG. 1 shows a variably expandable, two-piece suture anchor;

FIG. 1A is a proximal end view of an outer, expandable member of the suture anchor of FIG. 1, taken along lines 1A—1A;

FIG. 4 shows another variably expandable, two-piece suture anchor, with the expandable member shown in cross-section;

FIG. 4A is an end view of the suture anchor of FIG. 4, taken along lines 4A—4A;

FIG. 5 shows the suture anchor of FIG. 4 and a drive tool;

DESCRIPTION OF THE PREFERRED EMBODIMENTS

Figure 1B:
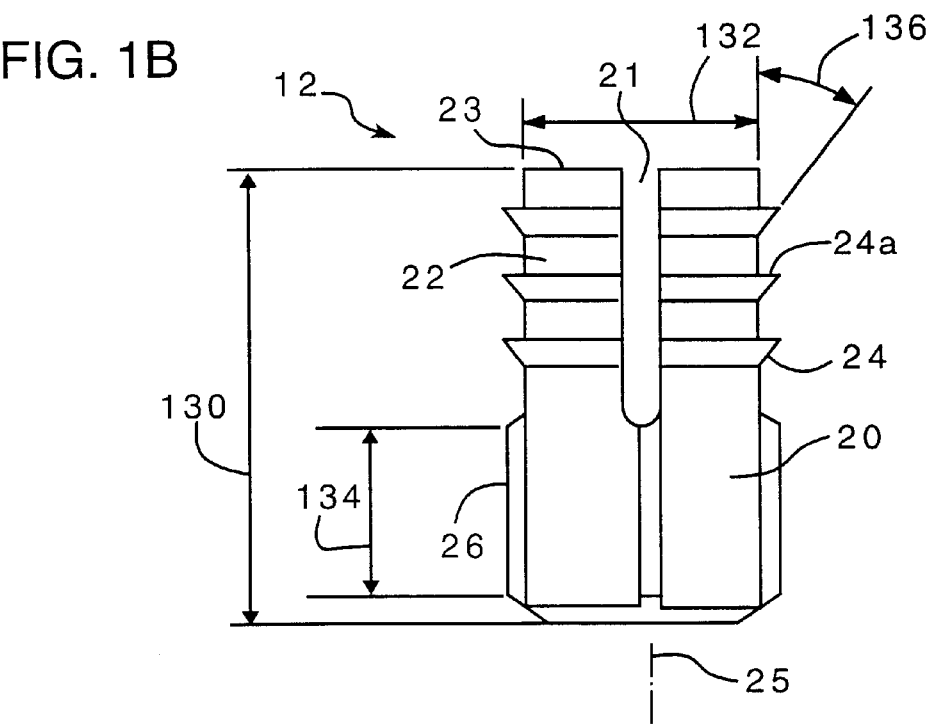
FIG. 1B is a side view of the expandable member of FIG. 1A.
Figure 1C:
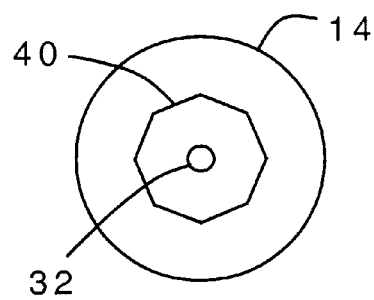
FIG. 1C is a proximal end view of an inner member of the suture anchor of FIG. 1, taken along lines 1C—1C.

Referring to FIGS. 1–1C, adjustably expandable suture anchor 10 includes an outer expandable anchoring member 12 and an inner member 14 which serves as a plunger that can be secured in any one of a plurality of positions within a cylindrical axial bore 16 in outer member 12. As will be described in more detail below, the insertion of inner member 14 causes outer member 12 to expand by an amount that corresponds to the position in which inner member 14 is inserted into outer member 12.

Outer and inner members 12, 14 may be made from bioabsorbable material, or not. If bioabsorbable, members 12, 14 can be made from any suitable copolymer, e.g., polyglyconate or PLA (polylactic acid). Suitable nonbioabsorbable materials include plastic polymers such as polyacetals (e.g., Delrin™ which is commercially available from duPont Corporation) and polyethylene, and metals such as titanium and stainless steel. If desired, outer and inner members 12, 14 can be made from different materials.

Outer member 12 includes a tubular body 20 at its distal end through which axial bore 16 passes. A portion of bore 16 is threaded 18 within body 20. A set of, e.g., four expansion arms 22 are integrally formed with body 20 and are arranged around bore 16. Arms 22 extend axially from body 20 to the proximal end of outer member 12. Put another way, arms 22 are cantilevered from body 20, and the free proximal ends 23 of arms 22 define the proximal end of bore 16. Expansion arms 22 are circumferentially spaced around the periphery of body 20 by axially extending slots 21 for purposes to be explained.

A series of (e.g., three) retention ridges 24 oriented transversely to the longitudinal axis 25 of outer member 12 are formed on the exterior surface of arms 22. Transverse ridges 24 are axially spaced from each other along arms 22. As shown in FIG. 1B, transverse ridges 24 include an inclined distal edge to ease insertion of outer member 12 into the bone, and a straight proximal edge 24a to resist pull out of outer member 12 from the bone. Body 20 includes a series of (e.g., four) axially-oriented ridges 26 on its exterior surface. Axial ridges 26 each includes an inclined edge and a flat edge 27 and are circumferentially aligned with slots 21 (FIG. 1A). As discussed in more detail below, axial ridges 26 resist rotation of outer member 12 in the bone.

FIG. 1B shows the exterior of outer member 12 in detail. The overall length of outer member 12 is approximately 0.35 inches, and the outer diameter 132 of body 20 and arms 22 is approximately 0.177 inches. Transverse and axial ridges 24, 26 each protrude approximately 0.015 inches from the exterior surfaces of arms 22 and body 20, respectively. Axial ridges 26 have a length 134 of about 0.133 inches. The inclined distal edges of transverse ridges 24 form an angle 136 at about 36° with longitudinal axis 25.

Inner member 14 (FIGS. 1 and 1C) includes a threaded distal section 28 with a blunt distal tip 28a which passes through bore 16 and engages threads 18 in outer member body 20. The proximal region 29 of inner member 14 is enlarged with respect to the interior diameter of bore 16 with a conically-shaped head 30. The exterior surfaces 31 of head 30 are tapered along axis 25 to provide a maximum diameter at the proximal end of inner member 14. A hexagonal socket 40 (FIG. 1C) is formed in head 30 for receiving a drive tool 42 (FIG. 2) used to insert inner member 14 into outer member 12, as will be explained.

An axial passage 32 is formed along longitudinal axis 25 through inner member 14 to provide a suture mount. Passage 32 receives suture 34 via an open proximal end in the radial center of socket 40 (FIG. 1C). Suture 34 passes completely through inner member 14 and emerges at an open distal end of passage 32 adjacent distal tip 28a of inner member 14. The distal region 36 of passage 32 has an enlarged width with respect to proximal regions 37 of passage 32. Preferably, distal region 36 tapers to the narrower width of proximal region 37, but distal region 36 can alternatively step down in size. During use, a knot 38 formed in suture 34 can be retracted into enlarged distal end 36 of passage 32 (by pulling suture 34 proximally in the direction of arrow 39). Among other advantages (discussed below), distal end 28 surrounds knot 38 and protects it from being damaged by the interference fit between suture anchor 10 and the bone.

Figure 2:
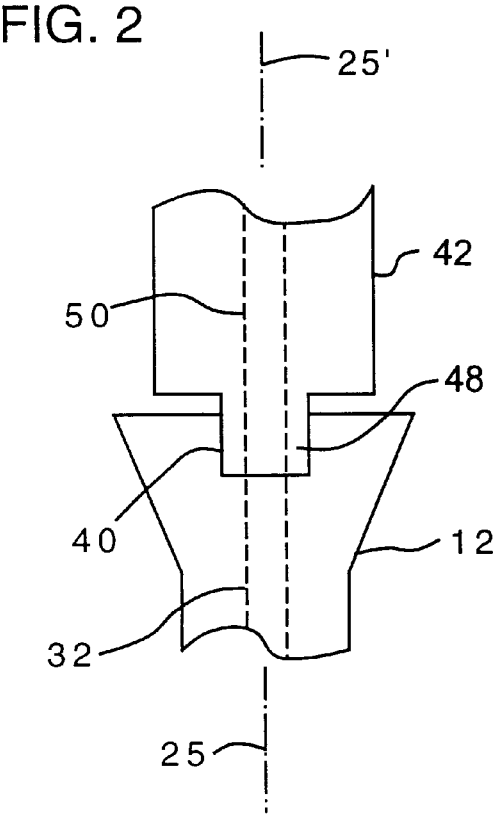
FIG. 2 shows a drive tool used to insert the inner member into the expandable member of the FIG. 1 suture anchor.

Referring to FIG. 2, drive tool 42 includes a hexagonal post 48 on its distal end which mates with socket 40 of insert member 14. The engagement between socket 40 and post 48 allows driver 42 to transmit insertion forces (in this example, torque) to rotate inner member 42. An internal suture tunnel 50 passes through drive tool 42 and post 48 and communicates with suture receiving passage 32 of inner member 12. Suture tunnel 50 is disposed on the longitudinal axis 25' of drive tool 42, which is aligned with inner member longitudinal axis 25 when post 48 is inserted into socket 40. As a result, when drive tool 42 is used to thread inner member 14 into outer member 12, drive tool 42, inner member 14, and suture 34 all rotate with respect to outer member 12. This avoids twisting and possibly damaging suture 34.

Figure 3:
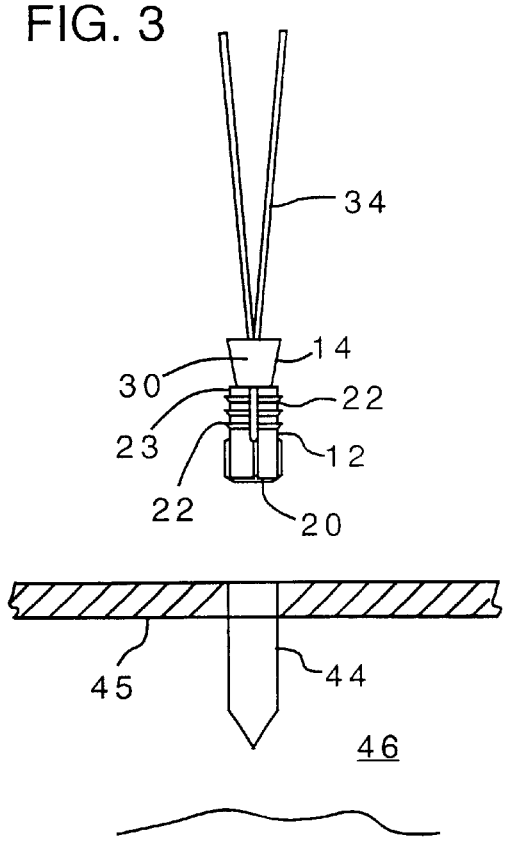
FIGS. 3–3B illustrate how the suture anchor of FIG. 1 is inserted into bone.
Figure 3A:
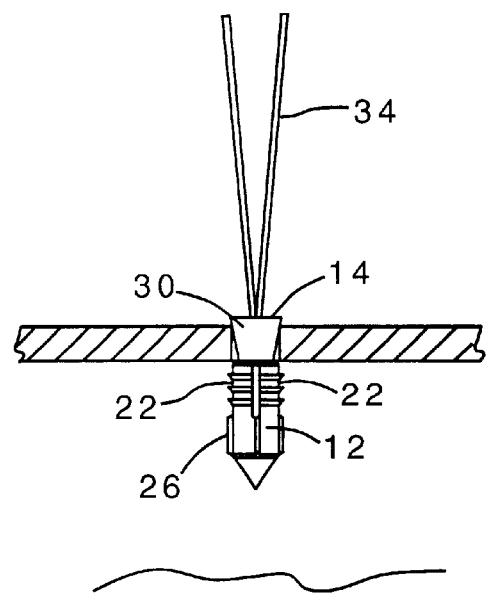
Figure 3B:
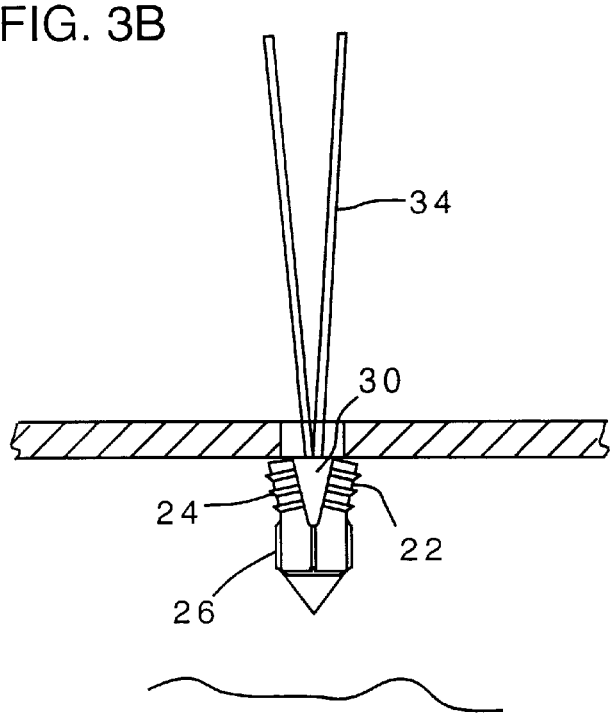

Referring to FIGS. 3–3B, suture anchor 10 is inserted and expanded in a pre-drilled hole 44 in bone tissue 46 as follows. (Drive tool 42 is not shown in FIGS. 3–3B for ease of illustration). As a preliminary step, suture 34 is passed through the drive tool and through axial passage 32 in insert member 14, and is knotted 38 (FIG. 1). Suture 34 is then pulled proximally (arrow 39), thereby retracting suture knot 38 into the enlarged distal end 36 of passage 32. The user then uses drive tool 42 (or his or her hands) to partially thread inner member 14 into outer member 12 until enlarged head 30 is positioned against (or slightly proximally of) the proximal end of outer member 12. Suture anchor 10 now has the configuration shown in FIG. 3.

Next, suture anchor 10 is inserted into pre-drilled hole 44. Depending upon the quality of bone tissue 46, hole 44 should be either the same diameter as or slightly narrower than the diameter of the cylindrical exterior surface of outer member 12. This provides an initial interference fit between outer member 12 and bone tissue 46 which, among other advantages, helps avoid outer member 12 rotating in hole 44 when inner member 14 is rotated further into outer member 12 to expand outer member 12. Preferably, bone hole 44 is sufficiently deep to enable outer member 12 to be installed (and thus be expanded) below in the cancellous bone beneath cortical bone 45, though this is not required. Indeed, cortical bone 45 need not be present and can even be removed (as is sometimes done in rotator cuff surgery) before outer member 12 is inserted.

Drive tool 42 is then used to rotate inner member 14 within outer member 12 to progressively advance inner member 14 axially into outer member 12. The engagement between threaded distal region 28 of inner member 14 and threads 18 of outer member body 20 allows the user to advance inner member 14 to any selected axial position within outer member 12 by rotating inner member 14 by a corresponding amount. Axial ridges 26 help avoid outer member 12 rotating within hole 44 as inner member is being threaded into outer member 12 (specifically, rotation is resisted by the engagement between flat edges 27, FIG. 1A, and bone tissue).

As inner member 14 advances distally, the tapered exterior surfaces 31 of enlarged head 30 engage the interior surfaces of arms 22, thereby causing arms 22 to expand radially outwardly. The amount by which arms 22 are radially expanded corresponds to the amount in which inner member 14 is inserted into outer member 12. For example, initially, when only proximal ends 23 of arms 22 are engaged by head 30, arms 22 are urged outwardly by a relatively small amount. But as inner member 14 is advanced distally in bore 16, head 30 engages arms 22 more distally, thereby causing arms 22 to be flared further outwardly (FIG. 3B).

As a result, the user can tailor the amount of expansion to provide the proper amount of fixation for procedure at hand. One way in which the user can control the amount of expansion is by using a torque meter to measure the force applied by drive tool 42. For example, the user sets a maximum torque level in advance according to the amount of fixation desired, and then inserts inner member 14 until this torque level is achieved. Accordingly, the amount of expansion will be a function of bone density. For example, when used in relatively soft bone tissue in which more fixation strength is desired (e.g., the greater tuberosity of the humerus during rotator cuff repairs), suture anchor 10 is expanded to a greater degree than might be required in harder bone tissue to obtain the same torque measurement.

The user advances inner member 14 until the desired amount of expansion is achieved (FIG. 3B). Drive tool 42 is then withdrawn, and suture 34 is ready for attachment to tissue (such as a ligament, tendon, or cartilage). The forces exerted between enlarged head 30 and bone tissue 46 through expanded outer member 12, as well as the threaded engagement with outer member 12, help retain inner member 14 in its inserted position and avoid inner member 14 "backing out" of outer member 12. Also, particularly when inner member 14 is made from a plastic, knot 38 (FIG. 1) may distend the distal walls of inner member 14 adjacent to opening 36 in response to pulling forces applied to suture 34, thereby further assisting in retaining inner member 14 in place. In addition to the expansion of outer member 12, transverse ridges 24 (and specifically the flat edges 24a, FIG. 1B, thereof) help retain suture anchor 10 within bone tissue 46 and resist pull-out in response to forces applied to suture 34.

Suture anchor 10 can be subsequently removed, if desired, by withdrawing inner member 14 using drive tool 42. Outer member 12 can then be collapsed radially using a suitable tool and extracted from bone tissue 46.

Other embodiments are within the scope of the following claims.

For example, outer and inner members 12, 14 can have other suitable configurations. More or fewer expansion arms 22 or transverse and axial ridges 24, 26 may be provided, as desired. Body 20 may also be equipped with transverse ridges 24. Proximal edges 24a of ridges 24 (FIG. 1B) can be back-cut to aid in retention.

The bone hole in which the suture anchor is mounted need not have cylindrical sides as illustrated. Instead, the hole can be tapered or have a stepped configuration. These alternatives may assist installing the suture anchor, and the variable expandability of the suture anchor helps ensure that suitable fixation strength will be obtained.

Other types of engagement between inner member 14 and drive tool 42 may be provided. For example, socket 40 (FIG. 1) can be, e.g., square-shaped rather than hexagonal. The positions of socket 40 and post 48 can be reversed.

The expansion-causing engagement of the inner and outer members need not be provided between a tapered conical head 30 and a cylindrical bore 16. For example, the configurations of bore 16 and head 30 can be reversed (e.g., the bore may be tapered and for engagement by a cylindrical head). Indeed, any arrangement which provides adjustable amounts of expansion will suffice.

Referring to FIGS. 4 and 4A, a suture anchor 60 includes an inner member 64 with a rib-shaped protrusion 76 near its proximal end for engaging and expanding an outer anchoring member 62. As with suture anchor 10, suture anchor 60 is assembled by threading inner member 64 into outer member 62. To this end, outer member 62 includes a cylindrical axial bore 66 that extends into a tubular body 70 at the distal end of outer member 62. Bore 66 is threaded 68 in body 70. A set of (e.g., four) circumferentially spaced arms 72 are integrally formed with body 70 and extend axially from body 70 to free ends at the proximal end of outer member 62. Arms 72 are spaced by axially extending slots 89 for purposes to be explained and include transverse ridges 74 on their exterior surfaces.

Inner member 64 includes a threaded distal section 79 with a pointed tip 79a which passes through bore 66 and engages threads 68 in outer member body 70. Rib 76 is located near the proximal end of inner member 64 and has an outer diameter which is greater than the diameter of bore 66. As a result, rib 76 engages arms 72 and causes arms 72 to progressively expand radially as inner member 64 is threaded into outer member 62.

The suture mount in suture anchor 60 is provided by a slot 78 which extends transversely through inner member 64 slightly distally of rib 76. A pair of axially extending channels 80 are formed in the exterior surface of inner member 64 between the proximal end 82 of inner member 64 and slot 78. Channels 80 are circumferentially aligned with the open ends of slot 78 and interrupt rib 76 (FIG. 4A) to provide passages for suture (not shown) which is passed through slot 78. This helps avoid damaging suture during the insertion of inner member 64 into outer member 62.

Referring also to FIG. 5, the proximal end 82 of inner member 64 is a hexagonally shaped post which mates with a drive tool 84. Drive tool 84 includes an inner shaft 81 which is rotatable within an outer sleeve 83. A hexagonally shaped socket 86 in the distal end of shaft 81 receives the hexagonal proximal end 82 of anchor inner member 64. Outer sleeve 83 extends distally of socket 86 and terminates in a set of (e.g., four) extension fingers 87 which are sized to be received in the axial slots 89 of anchor outer member 62 (FIG. 4). Drive tool 84 includes openings, not shown (e.g., along the sides of shaft 81 or through the interior thereof) through which suture is passed to inner member 62.

As with suture anchor 10, during use suture anchor 60 is inserted into a pre-drilled bone hole. (Alternatively, pointed tip 79a allows suture anchor 60 to be driven directly into the bone without first forming a bone hole). After suture has been threaded through slot 78 and channels 80, inner member 64 is partially threaded into outer member 62 until rib 76 is disposed slightly proximally of arms 72. Suture anchor 60 is then installed in the bone hole using drive tool 84. An exterior shoulder 85 positioned proximally of the distal end of sleeve 83 limits the depth to which suture anchor 60 can be inserted.

To expand suture anchor 60, the user holds outer sleeve 83 firmly in place and rotates inner shaft 81. The engagement of fingers 87 within slots 89 keeps outer member 62 stationary, and thus the rotation of inner shaft 81 advances inner member 64 distally into outer member 62. Rib 76 engages arms 72 and causes arms 72 to expand radially outwardly as inner member 64 advances. As with suture anchor 10, the amount of expansion corresponds to the amount in which inner member 64 is inserted into outer member 62.

A drive tool similar to drive tool 84 can be used to install suture anchor 10 (FIG. 1). In this case, extension fingers 87 would be received by slots 21 in outer member 12, and inner shaft 81 would include a hexagonal post (rather than a socket) to engage and rotate inner member 14.

Figure 6:
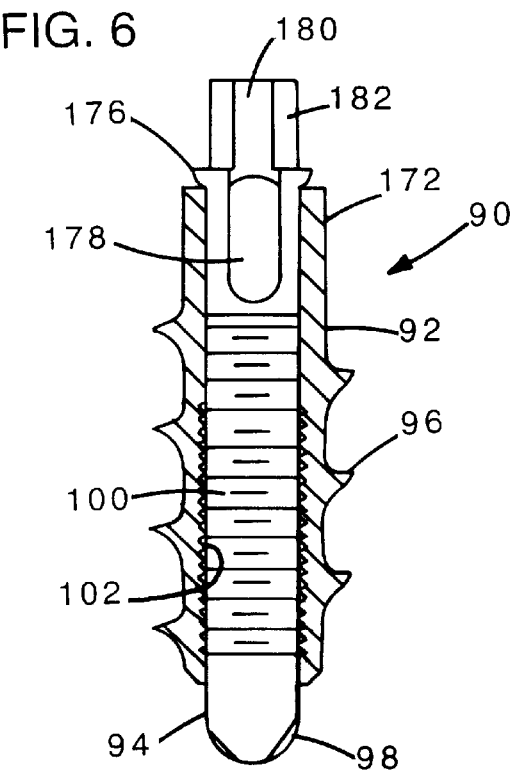
FIG. 6 shows yet another variably expandable, two-piece suture anchor, with the expandable member shown in cross-section.
Figure 7:
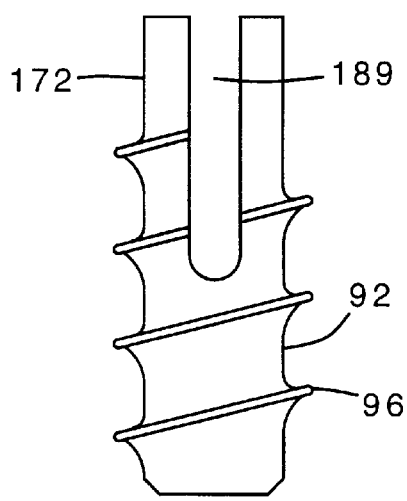
FIG. 7 is a side view of the expandable member of the suture anchor of FIG. 6.

Referring to FIGS. 6 and 7, adjustably expandable suture anchor 90 is "self-tapping" into bone, and thus does not require a pre-drilled bone hole. Expandable outer member 92 (which is advantageously made from stainless steel in this embodiment) includes screw threads 96 on its exterior surface to enable outer member 92 to be threaded through the bone surface. In addition, inner member 94 includes a screw-tip 98 at its distal end to aid in self-tapping.

Any of the adjustable expansion techniques described herein can be used to cause inner member 94 to selectively expand outer member 92. In the example shown, inner member 94 includes a rib 176 near its proximal end 182 similar to that of suture anchor 60.

The proximal end 182 of inner member 94 is hexagonal in shape to receive inner shaft 81 of drive tool 84 (FIG. 5). Inner member 94 also includes a transverse suture passage 178 and a pair of axially extending channels 180 similar to those discussed above for suture anchor 60. The distal end of inner member 94 is threaded 100 and engages interior threads 102 in the distal region of outer member 92. A set of (e.g., four) axially extending expansion arms 172 are integrally formed with the threaded distal region of outer member 92. Arms 172 are spaced by axial slots 189 (FIG. 7) which receive drive tool extension fingers 87 (FIG. 5).

Suture anchor 90 is inserted and expanded in the bone as follows. First, suture anchor 90 is assembled to the extent shown in FIG. 6 and threaded with suture (not shown). Next, outer member 92 is installed onto the distal end of drive tool outer sleeve 83 (FIG. 5) by sliding extension fingers 87 into slots 189, and outer sleeve 83 is used to thread outer and inner members 92, 94 together into the bone. Then, outer sleeve 83 is held stationary, and inner shaft 83 is rotated to advance inner member 94 within outer member 92. Rib 176 engages and radially expands arms 172 as inner member 94 is advanced distally into outer member 92 until the selected amount of expansion is achieved. External threads 96 serve as retention ridges to help resist pull-out of anchor 90 from the bone.

Other ways of inserting the inner member into the outer member are possible.

Figure 8:
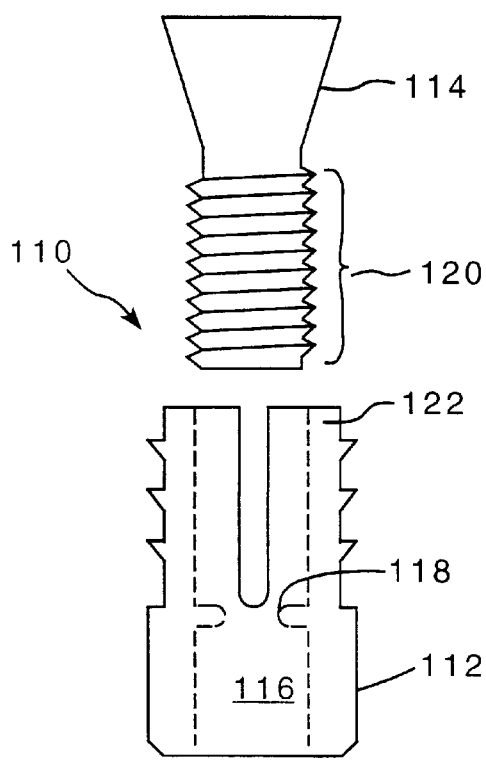
FIG. 8 shows still another variably expandable, two-piece suture anchor.

For example, referring to FIG. 8, suture anchor 110 includes a ratchet-like mechanism for progressive insertion and retention of inner member 114 into outer expandable anchoring member 112. Outer member 112 includes a bore 116 with a protrusion 118 (or a set of circumferentially spaced protrusions 118), preferably a circumferential protrusion. Inner member 114 includes spaced circumferential grooves 120 which "lock" with protrusion 118 as inner member 114 is axially pushed (rather than rotated) into bore 116. The ratchet-like mechanism permits purely axial insertion of inner member 114 and retention of inner member 114 at a desired position to control the amount of expansion of arms 122 (i.e., inner member 114 need not be rotated to progressively insert it into bore 116).

Suture anchor 110 can include any of the suture mounts discussed herein. For example, head 114 may be equipped with a transverse hole and a pair of axial channels similar to those shown in FIG. 4 for receiving suture. Alternatively, of course, the axially-oriented suture mount of FIG. 1 can be used.

Figure 9:
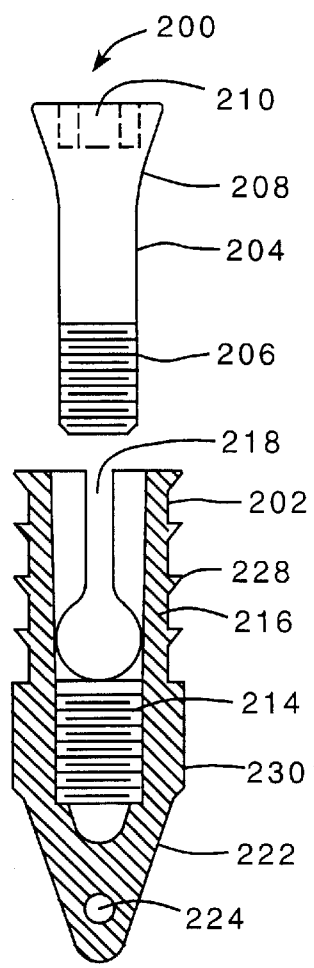
FIGS. 9–9B illustrate yet another variably expandable, two piece suture anchor.
Figure 9A:
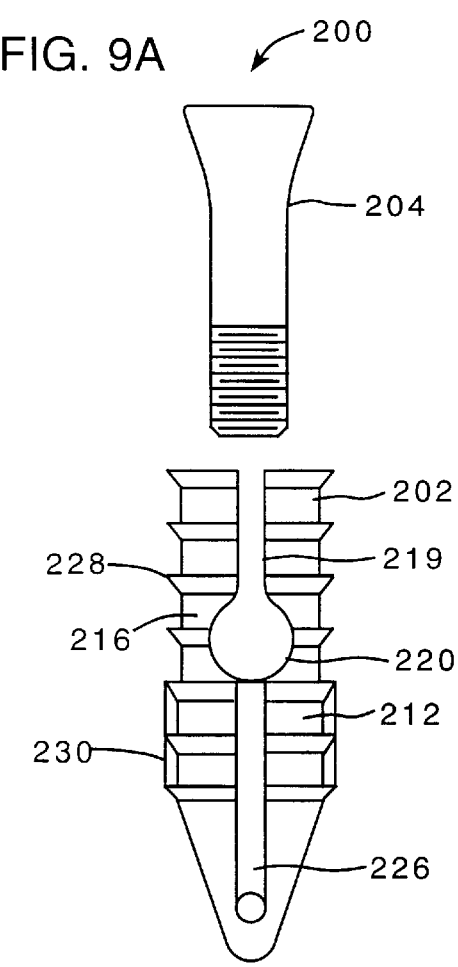
Figure 9B:
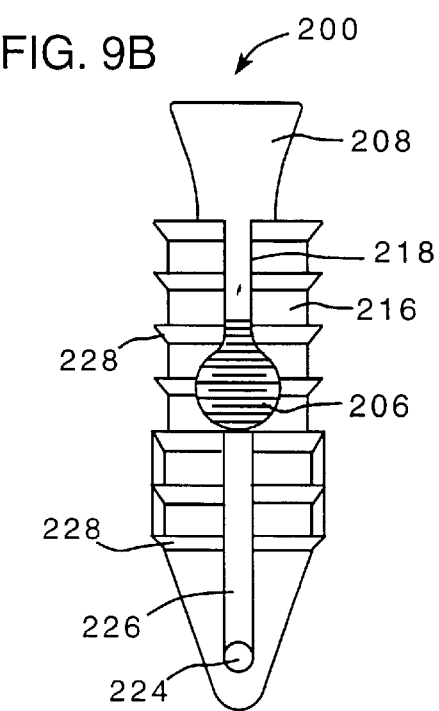

Referring to FIGS. 9–9B, another adjustably expandable suture anchor 200 includes an expandable outer anchoring member 202 and an inner member 204 which is threaded into outer member 202 to adjustably expand outer member 202 in a manner similar to that described above for suture anchors 10, 60, and 90. Inner member 204 is similar to inner member 10 (FIG. 1) and includes a threaded distal section 206 with a blunt tip, and an enlarged, conically-shaped proximal head 208. The proximal end of inner member 204 includes a hexagonally-shaped opening 210 that receives a drive tool.

Outer member 202 includes a tubular body 212 with an interior, threaded bore 214 which is engaged by threaded inner member section 208. A pair of arms 216 extend axially and proximally from body 212 to the proximal end of outer member 202. Body 212 and arms 216 are integrally formed as a single unit. Arms 216 are circumferentially spaced around the periphery of outer member 202 by a pair of keyhole-shaped slots 218 which are separated by 180 degrees. Each slot 218 has a relatively narrow neck 210 that extends axially from the proximal end of outer member and terminates in an enlarged aperture 220 adjacent to the junction between body 212 and arms 216. Using only two arms 216 increases the surface contact with the bone tissue, which enhances retention. Enlarged apertures 220 help ensure that arms 216 are sufficiently flexible at body 212 to expand radially.

The distal end 222 of outer member 202 is closed and defines a tapered tip. A suture mount in the form of an opening 224 is formed through distal end 222 transversely to the longitudinal axis of outer member 202. The ends of opening 224 are open and are circumferentially aligned with a pair of suture-receiving channels 226 in the exterior surface of outer member 202. Channels 226 are in turn circumferentially aligned with keyhole-shaped slots 218 to provide a passage for suture which is passed through opening 224.

A series of (e.g., seven) axially spaced, transversely oriented ridges 228 are formed on the exterior surface of body 212 and arms 216. Transverse ridges 228 help retain suture anchor 200 within bone by providing an interference fit with the bone tissue. Outer member 202 also includes a pair of axially extending ridges 230 which protrude from the exterior surface of body 212. Such axial ridges 230 frictionally engage the walls of a bone hole to resist rotation of outer member 202 when inner member 204 is being inserted into outer member 202.

In use, with outer and inner members 202, 204 assembled as shown in FIG. 9B (and with suture, not shown, passed through opening 224), suture anchor 200 is inserted into a bone hole. Inner member 204 is then threaded into outer member 202 so that conical head 208 engages arms 216 and urges arms 216 to expand radially outwardly into the bone.

The enlarged apertures 220 of slots 218 both facilitate the expansion of arms 216 and help ensure that arms 216 flex at the locations of apertures 218 rather than more proximally. As with previously-discussed embodiments, the amount of expansion corresponds to the amount in which inner member 204 is advanced distally into outer member 224.

The driver (not shown) used to advance inner 202 engages the proximal end of outer member 202 to drive outer member 202 into a bone hole. A rotatable driving element (also not show) is used to thread inner member 204 into outer member 202. Axial ridges 230 keep outer member 202 stationary as inner member 204 is being advanced.

Because outer member 202 includes two rather than four arms, the expanded outer member 202 is oval or elliptical in shape when viewed from above. Put another way, outer member 202 does not expand in the direction of slots 218 and thus does not damage suture lying within slots 218. The suture is also protected during the insertion of suture anchor 200 into the bone and while inner member 204 is being advanced into outer member 202 by channels 226.

What is claimed is:

1. A suture anchor comprising
a pair of members constructed to dwell within tissue, one of said members including a suture mount,
said members each including a locking element for securing the members together in a selected one of a plurality of positions, each of the plurality of positions causing an expansion of a first one of said member by a differing amount such that when secured together the first one of said members expands by an amount that corresponds to the selected position.

2. The suture anchor of claim 1 wherein said first one of said members comprises an outer member having an opening therein, a second one of said members comprising an inner member progressively insertable into said opening to be secured to said outer member in said selected one of said plurality of positions.

3. The suture anchor of claim 2 wherein said outer member includes a body configured to be secured to said inner member and an expandable portion configured to be expanded by said inner member, said opening being disposed through said expandable portion and said body along a longitudinal axis of said outer member.

4. The suture anchor of claim 3 wherein said expandable portion includes a plurality of arms which extend axially from said body to a proximal end of said outer member.

5. The suture anchor of claim 4 wherein said inner member is configured for insertion into said opening at said proximal end of said outer member and includes an enlargement for engaging said arms and causing said arms to progressively expand radially outwardly as said inner member is inserted distally into said opening.

6. The suture anchor of claim 5 wherein said enlargement is disposed on a portion of an exterior surface of said inner member and tapers in size axially along said inner member.

7. The suture anchor of claim 6 wherein said enlargement comprises a conically shaped proximal end of said inner member.

8. The suture anchor of claim 5 wherein said enlargement comprises a rib disposed on a portion of an exterior surface of said inner member.

9. The suture anchor of claim 4 wherein said arms are arranged around a periphery of said outer member and are circumferentially spaced by axially extending slots.

10. The suture anchor of claim 9 wherein each of said slots includes an enlarged portion adjacent to a junction between said arms and said body.

11. The suture anchor of claim 4 further comprising a ridge disposed on an exterior surface of said arms and oriented transversely to said axis.

12. The suture anchor of claim 4 further comprising a ridge disposed on an exterior surface of said body and oriented along said axis.

13. The suture anchor of claim 3 wherein said outer member locking element comprises threads in said opening in said body, and said inner member locking element comprises threads at a distal region of said inner member for threadably engaging said body to secure said inner member to said outer member in said selected one of said plurality of positions.

14. The suture anchor of claim 3 wherein said inner member and said outer member locking elements are configured for ratchet-like engagement therebetween as said inner member is axially inserted into said opening.

15. The suture anchor of claim 14 wherein said inner member locking element comprises circumferential grooves arranged axially along an exterior surface of said inner member, and said outer member locking element comprises a projection in said body opening to progressively engage said grooves as said inner member is axially inserted into said opening.

16. The suture anchor of claim 3 wherein said opening terminates in a closed distal end of said body.

17. The suture anchor of claim 16 wherein said closed distal end forms a tapered tip.

18. The suture anchor of claim 16 wherein said suture mount includes a suture receiving passage in said closed distal end oriented transversely to a longitudinal axis of said outer member.

19. The suture anchor of claim 18 wherein said passage includes a pair of open ends in an exterior surface of said distal end, and further comprising a pair of axially oriented channels in said exterior surface adjacent to said open ends.

20. The suture anchor of claim 18 wherein said expandable portion includes a plurality of arms which extend axially from said body to a proximal end of said outer member, said arms being arranged around a periphery of said outer member and being circumferentially spaced by axially extending slots that are aligned with said channels.

21. The suture anchor of claim 2 wherein said outer member is configured for insertion into a pre-drilled bone hole.

22. The suture anchor of claim 2 wherein said outer member includes threads on an exterior surface thereof.

23. The suture anchor of claim 2 wherein said suture mount comprises a suture receiving passage in said inner member and arranged along a longitudinal axis of said inner member.

24. The suture anchor of claim 23 wherein said suture receiving passage has an enlarged portion at a distal end of said inner member.

25. The suture anchor of claim 24 wherein said enlarged portion tapers in width proximally along said longitudinal axis.

26. The suture anchor of claim 2 wherein said suture mount includes suture receiving passage in said inner member and disposed transversely to a longitudinal axis of said inner member.

27. The suture anchor of claim 26 wherein said passage includes a pair of open ends in an exterior surface of said inner member, and further comprising a pair of axially oriented channels in said exterior surface adjacent to said open ends.

28. The suture anchor of claim 2 wherein said suture mount is disposed on said outer member.

29. A suture anchor comprising
an outer member which includes a body with an axially extending, threaded opening therein which terminates at a closed distal end of said body, and a plurality of arms arranged about the periphery of said body and extending axially from said body to a proximal end of said outer member,
a suture mount including a suture receiving passage in said closed distal end oriented transversely to a longitudinal axis of said outer member, and
an inner member having a threaded distal end configured to be inserted into said opening and threadably engage said body, and an enlargement on a proximal region thereof configured to engage said arms and cause said arms to be expanded radially by a selected amount that corresponds to an amount by which said distal end is inserted into said opening.

30. The suture anchor of claim 29 wherein said enlargement comprises a conically shaped proximal end of said inner member.

31. The suture anchor of claim 29 wherein said enlargement comprises a rib disposed on a portion of an exterior surface of said inner member.

32. The suture anchor of claim 29 wherein said suture receiving passage has a pair of open ends in an exterior surface of said distal end, and further comprising a pair of axially oriented channels in said exterior surface adjacent to said open ends of said passage.

33. The suture anchor of claim 29 wherein said arms are circumferentially spaced by axially extending slots that are aligned with said channels, each of said slots having an enlarged portion adjacent to a junction between said arms and said body.

34. The suture anchor of claim 29 further comprising a plurality of axially spaced ridges disposed on an exterior surface of said arms and oriented transversely to a longitudinal axis of said outer member.

35. The suture anchor of claim 29 further comprising a plurality of circumferentially spaced ridges disposed on an exterior surface of said body and oriented along a longitudinal axis of said outer member.

36. Apparatus comprising
a suture anchor that includes
an outer member and an inner member, one of which has a suture mount,
said outer member having an opening therein and said members each including a locking element for securing said inner member to said outer member in a selected one of a plurality of positions in said opening, each of the plurality of positions causing an expansion of said outer member by a differing amount such that when secured together said outer member expands by an amount that corresponds to the selected position; and
a driver configured to engage said inner member and insert said inner member into said opening and secure said inner member at said selected position.

37. The apparatus of claim 36 wherein
said an outer member includes a body having an axially extending opening therein, and a plurality of arms which extend axially from said body to a proximal end of said outer member, said arms being arranged around a periphery of said body, and said inner member has a distal end including said locking element for securing said inner member to said outer member within said opening in said selected one of said plurality of positions, and an enlargement on a proximal region thereof configured to engage said arms, said driver and said proximal region of said inner member being configured to engage each other so that said driver can transmit force to said inner member to progressively insert said distal region into said opening and cause said enlargement to engage and radially expand said arms by a selected amount that corresponds to an amount by which said distal end is inserted into said opening.

38. The apparatus of claim 37 wherein said outer member locking element comprises threads in said opening of said outer member and said inner member locking element comprises threads, said proximal region of said inner member and said driver being configured to enable said driver to rotate said inner member to progressively insert said inner member into said outer member.

39. The apparatus of claim 38 wherein said proximal region includes a socket and said driver includes a post configured to be received by said socket.

40. The apparatus of claim 39 wherein said suture mount includes a suture receiving passage disposed in said inner member along a longitudinal axis thereof, said passage having an open end disposed in said socket, said driver having an passage disposed therein and arranged to communicate with said suture receiving passage when said post is received in said socket.

41. The apparatus of claim 38 wherein
said outer member of said suture anchor includes a plurality of axially extending slots between said arms, and
said driver includes an outer sleeve with a distal end configured to be received by said slots, and a rotatable inner shaft disposed within an outer sleeve and configured to engage said proximal region of said inner member of said suture anchor.

42. The apparatus of claim 41 further comprising an exterior shoulder positioned on said outer sleeve at a selected distance proximally of said distal end thereof.

43. A method of inserting a suture anchor into bone, comprising
providing a suture anchor that includes a pair of members constructed to dwell within tissue, one of said members including a suture mount, said members each including a locking element for securing the members together in a selected one of a plurality of positions,
implanting a first one of said members into the bone, and
securing a second one of the members to said first member in a selected one of a plurality of positions, each of the plurality of positions causing an expansion of said first member by a differing amount such that when secured together said first member expands by an amount that corresponds to the selected position.

44. The method of claim 43 wherein said securing step includes progressively inserting said second member into an opening in said first member and securing said second member in said selected one of said plurality of positions in said opening.

45. The method of claim 44 wherein each of said locking elements comprises threads and said step of progressively inserting includes threading said second member into said opening.

46. The method of claim 45 further comprising preselecting a threshold amount of force to be exerted on said second member during said inserting, measuring said force during said inserting of said second member, and stopping said inserting member when said threshold is reached.

47. The method of claim 43 wherein said step of implanting includes forming a hole in the bone and then installing said first member into said hole.

48. The method of claim 43 wherein said step of implanting includes threadably inserting said first member into the bone.

49. The method of claim 43 wherein said step of implanting includes preassembling said first member and said second member and inserting them as a unit into the bone.

50. A suture anchor comprising
a pair of members one of which includes a suture mount,
said members being configured to be secured together in a selected one of a plurality of relative axial positions to cause a first one of said members to expand by an amount that corresponds to the selected axial position,
said first one of said members comprising an outer member having an opening therein, a second one of said members comprising an inner member progressively axially insertable into said opening to be secured to said outer member in said selected one of said plurality of relative axial positions,
said outer member including a body configured to be secured to said inner member and an expandable portion configured to be expanded by said inner member, said expandable portion including a plurality of arms which extend axially from said body to a proximal end of said outer member.

51. The suture anchor of claim 50 wherein said inner member is insertable into said opening at said proximal end of said outer member and includes an enlargement which engages said arms and causes said arms to progressively expand radially outwardly as said inner member is inserted distally into said opening.

52. A suture anchor comprising
a pair of members one of which includes a suture mount,
said members being configured to be secured together in a selected one of a plurality of positions to cause a first one of said members to expand by an amount that corresponds to the selected position,
said first one of said members including an outer member having an opening therein, a second one of said members including an inner member progressively insertable into said opening to be secured to said outer member in said selected one of said plurality of positions,
said outer member including a body configured to be secured to said inner member and an expandable portion configured to be expanded by said inner member, said opening being disposed through said expandable portion and said body along a longitudinal axis of said outer member, said expandable portion including a plurality of arms which extend axially from said body to a proximal end of said outer member, said arms being arranged around a periphery of said outer member and circumferentially spaced by axially extending slots, each of said slots including an enlarged portion adjacent to a junction between said arms and said body.

53. A suture anchor comprising
a pair of members one of which includes a suture mount,
said members being configured to be secured together in a selected one of a plurality of positions to cause a first one of said members to expand by an amount that corresponds to the selected position,
said first one of said members including an outer member having an opening therein, a second one of said members including an inner member progressively insertable into said opening to be secured to said outer member in said selected one of said plurality of positions, said outer member including a body configured to be secured to said inner member and an expandable portion configured to be expanded by said inner member, said opening being disposed through said expandable portion and said body along a longitudinal axis of said outer member, said expandable portion including a plurality of arms which extend axially from said body to a proximal end of said outer member, said body including a ridge disposed on an exterior surface of said body and oriented along said axis.

54. A suture anchor comprising an outer member which includes a body with an axially extending, threaded opening therein which terminates at a closed distal end of said body, a plurality of arms arranged about the periphery of said body and extending axially from said body to a proximal end of said outer member, and a plurality of circumferentially spaced ridges disposed on an exterior surface of said body and oriented along a longitudinal axis of said outer member, a suture mount including a suture receiving passage in said closed distal end oriented transversely to a longitudinal axis of said outer member, and an inner member having a threaded distal end configured to be inserted into said opening and threadably engage said body, and an enlargement on a proximal region thereof configured to engage said arms and cause said arms to be expanded radially by a selected amount that corresponds to an amount by which said distal end is inserted into said opening.

55. A method of inserting a suture anchor into bone, comprising providing a suture anchor that includes a pair of members one of which includes a suture mount, disposing a first one of said members into the bone, and progressively inserting a second one of the members into an opening in said first member and securing said second member by threading said second member into said opening, preselecting a threshold amount of force to be exerted on said second member during said inserting, measuring said threshold during said inserting of said second member, said inserting stopping when said threshold is reached, and securing said second member to said first member in a selected one of a plurality of positions to cause said first member to expand by an amount that corresponds to the selected position.

56. A suture anchor comprising:

a pair of members one of which includes a suture mount, said members each including a locking element for securing the members together in a selected one of a plurality of relative axial positions, each of the plurality of relative axial positions causing an expansion of a first one of said member by a differing amount such that when secured together the first one of said members expands by an amount that corresponds to the selected axial position.

57. The suture anchor of claim 56, wherein said first one of said members comprises an outer member including a body, said outer member locking element comprising a threaded region of said body, a second one of said members comprising an inner member, said inner member locking element comprising a threaded region to threadably engage said body to secure said inner member to said outer member in said selected one of said plurality of axial positions.

58. A method of inserting a suture anchor into bone, comprising providing a suture anchor that includes a pair of members one of which includes a suture mount, said members each including a locking element for securing the members together in a selected one of a plurality of positions, implanting a first one of said members into the bone, securing a second one of the members to said first member in a selected one of a plurality of relative axial positions, each of the plurality of relative axial positions causing an expansion of said first member by a differing amount such that when secured together said first member expands by an amount that corresponds to the selected axial position.

59. The method of claim 58, wherein each said locking element comprises threads and said securing step includes threading said second member into an opening in said first member.

* * * * *